(12) United States Patent
Monget et al.

(10) Patent No.: US 8,334,112 B2
(45) Date of Patent: Dec. 18, 2012

(54) MEDIUM FOR DETECTING AND/OR IDENTIFYING BACTERIA

(75) Inventors: Daniel Monget, Saint Sorlin En Bugey (FR); Sylvain Orenga, Neuville sur Ain (FR); John Perry, Newcastle-Upon-Tyne (GB); Michel Peyret, Lyons (FR); Celine Roger-Dalbert, Chazay sur Ain (FR)

(73) Assignee: Biomerieux, Marcy l'Etoile (FR)

( * ) Notice: Subject to any disclaimer, the term of this patent is extended or adjusted under 35 U.S.C. 154(b) by 457 days.

(21) Appl. No.: 12/448,895

(22) PCT Filed: Feb. 7, 2008

(86) PCT No.: PCT/FR2008/050184
§ 371 (c)(1),
(2), (4) Date: Jul. 14, 2009

(87) PCT Pub. No.: WO2008/104680
PCT Pub. Date: Sep. 4, 2008

(65) Prior Publication Data
US 2010/0062467 A1  Mar. 11, 2010

(30) Foreign Application Priority Data
Feb. 8, 2007 (FR) .................................. 07 53150

(51) Int. Cl.
C12Q 1/10 (2006.01)
C12Q 1/04 (2006.01)
C12Q 1/02 (2006.01)
C12N 1/20 (2006.01)

(52) U.S. Cl. .... 435/34; 435/29; 435/252.1; 435/252.33; 435/849

(58) Field of Classification Search .................. None
See application file for complete search history.

(56) References Cited

U.S. PATENT DOCUMENTS

| | | | | | |
|---|---|---|---|---|---|
| 5,643,743 | A | * | 7/1997 | Chang et al. | 435/34 |
| 5,888,760 | A | * | 3/1999 | Godsey et al. | 435/34 |
| 6,146,840 | A | * | 11/2000 | Chang et al. | 435/14 |
| 2008/0160555 | A1 | * | 7/2008 | Rambach | 435/19 |

FOREIGN PATENT DOCUMENTS

| EP | 1 293 575 A2 | 3/2003 |
|---|---|---|
| WO | WO 91/18111 A1 | 11/1991 |
| WO | WO 2006/089889 * | 8/2006 |

OTHER PUBLICATIONS

Perry, J.D. et al. "Evaluation of a new chromogenic medium, Uriselect 4, for the isolation and identification of urinary tract Pathogens," *J. Clin. Pathol*, vol. 56, 2003, pp. 528-531.

Mazoyer, M. A. et al. "Evaluation of CPS ID2 Medium for Detection of Urinary Tract Bacterial Isolates in Specimens from a Rehabilitation Center," *Journal of Clinical Microbiology*, Apr. 1995, pp. 1025-1027.

Ciragil, P. et al. "Evaluation of a new chromogenic medium for isolation and identification of common urinary tract pathogens," *Eur. J. Clin. Microbiol Infect Dis.*, vol. 25, 2006, pp. 108-111.

Carricajo, A. et al. "Comparative Evaluation of Five Chromogenic Media for Detection, Enumeration and Identification of Urinary Tract Pathogens," *Eur. J. Clin. Microbiol Infect Dis*, vol. 18, 1999, pp. 796-803.

* cited by examiner

*Primary Examiner* — Vera Afremova
(74) *Attorney, Agent, or Firm* — Oliff & Berridge, PLC

(57) ABSTRACT

The invention relates to a method for detecting and/or identifying *Escherichia coli* (*E. coli*) in a biological sample, that comprises inoculating the biological sample liable to contain *E. coli* on a detection medium that comprises tryptophan and a substrate for an enzyme A, expressed by the majority of *E. coli*, in order to obtain bacterial colonies; detecting the colonies expressing the activity of the enzyme A and identifying them as being *E. coli*; and detecting the colonies that do not express the activity of the enzyme A, carrying out an indole test, and identifying the colonies having a positive indole test as being *E. coli*.

16 Claims, No Drawings

MEDIUM FOR DETECTING AND/OR IDENTIFYING BACTERIA

The field of the invention is that of biochemical microbiological analysis, and in particular of the detection and identification of bacteria.

Pathogenic bacteria, and in particular Gram-negative bacilli, such as enterobacteria, are responsible each year for many diseases, epidemics, etc.

The species *E. coli* (*Escherichia coli*) is the aerobic species most predominantly represented in the digestive tract. However, the presence of said bacteria in water indicates fecal contamination, and certain strains are pathogenic and responsible for peritoneal, biliary, appendicular or genital suppurations.

Early and specific detection of *E. coli* makes it possible to propose a suitable solution, in terms of treatment, of decontamination, etc. This detection can be based in particular on the use of detection media comprising particular substrates, specific for a metabolic activity, referred to as target metabolic activity, such as an enzymatic activity, of the bacterium that it is desired to detect: through the choice of substrates, depending on whether or not there is a reaction, it is possible to characterize the nature of a microorganism.

The CPS ID 3 medium (bioMerieux) uses a β-glucuronidase substrate combined with a β-glucosidase substrate and, optionally, with the detection of tryptophanase, for detecting strains of the *Escherichia coli* species. However, while this medium has excellent specificity, the use of a β-glucuronidase substrate for detecting *E. coli* exhibits imperfect sensitivity owing to the existence of a small proportion of *E. coli* strains (5-10%) which do not express this activity. Furthermore, certain *Citrobacter* strains can also produce β-glucuronidase-positive colonies, that are the same color as those of *E. coli*.

The invention proposes to solve the prior art problems by providing a new medium that is particularly suitable for identifying *E. coli* bacteria rapidly and inexpensively and in a manner that is easy to implement.

Surprisingly, the inventors have shown that a suitable supplementary test enables rapid and easy detection of *E. coli*. More specifically, the inventors have in particular shown that an indole test carried out on the *E. coli* that do not express the target metabolic activity makes it possible to increase the sensitivity of the test.

Before proceeding with the disclosure of the invention, the following definitions are given in order to facilitate the understanding of the invention.

The term biological sample is intended to mean a clinical sample, derived from a sample of biological fluid, or a food sample, derived from any type of food, or an environmental sample such as a surface sample, water sample, air sample, etc. This sample may thus be liquid or solid and mention may be made, in a nonlimiting manner, of a clinical sample from blood, plasma, urine or feces, samples taken from the nose, from the throat, from the skin, from wounds or from cerebrospinal fluid, a food sample from water, or from drinks such as milk or a fruit juice; from yogurt, meat, eggs, vegetables, mayonnaise or cheese; from fish, etc., or a food sample derived from an animal feed, such as in particular a sample derived from animal meals.

The term detection medium is intended to mean a medium comprising all the elements necessary for the survival and/or the growth of microorganisms. This detection medium can either serve as detection medium only, or as culture and detection medium. In the first case, the culturing of the microorganisms is carried out before seeding, and in the second case, the detection medium also constitutes the culture medium. The culture medium according to the invention may contain other possible additives, for instance: peptones or extracts of tissues, one or more growth factors, carbohydrates, one or more selective agents, buffers, one or more gelling agents, etc. This culture medium may be in liquid form or in the form of a ready-to-use gel, i.e. ready for seeding in a tube or flask or on a Petri dish.

For the purpose of the present invention, the detection can be carried out in liquid medium, a strip, or another solid support.

The term substrate is intended to mean any molecule capable of directly or indirectly generating a detectable signal due to an enzymatic or metabolic activity of the microorganism.

The substrate may in particular be a metabolic substrate, such as a carbon or nitrogen source, coupled to an indicator that produces a coloration in the presence of one of the products of the metabolism.

The substrate may also be an enzymatic substrate, i.e. a substrate that can be hydrolyzed by an enzyme so as to give a product that enables direct or indirect detection of a microorganism. This substrate may in particular comprise a first part which is specific for the enzymatic activity to be revealed and a second part which acts as a label, hereinafter known as label part. This label part may be chromogenic, fluorogenic, luminescent, etc. As chromogenic substrate suitable for solid supports (filter, agar, electrophoresis gel), mention may in particular be made of substrates based on indoxyl and its derivatives, and substrates based on hydroxyquinoline or on esculetin and their derivatives, which enable the detection of osidase and esterase activities. Mention may also be made of substrates based on nitrophenol and nitroaniline and derivatives, for detecting osidase and esterase activities in the case of nitrophenol-based substrates, and peptidase activities in the case of nitroaniline-based substrates. Finally, mention may be made of substrates based on naphthol and naphthylamine and their derivatives, which make it possible to detect osidase and esterase activities by means of naphthol, and peptidase activities by means of naphthylamine. This substrate may in particular, but in a nonlimiting manner, enable the detection of an enzymatic activity such as the activity of an osidase, peptidase, esterase, etc. The enzymatic substrate may also be a natural substrate, the product of hydrolysis of which is detected directly or indirectly. As a natural substrate, mention may in particular be made of tryptophan for detecting a tryptophanase or deaminase activity, a cyclic amino acid (tryptophan, phenylalanine, histidine, tyrosine) for detecting a deaminase activity, phosphatidylinositol for detecting a phospholipase activity, etc.

According to the present invention, the substrate is preferably selected from substrates based on indoxyl (3-indoxyl, 5-bromo-3-indoxyl, 5-iodo-3-indoxyl, 4-chloro-3-indoxyl, 5-bromo-4-chloro-3-indoxyl, 6-bromo-3-indoxyl, 6-fluoro-3-indoxyl, 5-bromo-4-chloro-n-methyl-3-indoxyl, n-methyl-3-indoxyl, etc.); based on umbelliferone (4-methylumbelliferone, cyclohexenoesculetin, etc.); based on alizarine; based on p-naphtholbenzein; based on nitrophenol (ortho-nitrophenol, para-nitrophenol, etc.); based on aminophenol (para-aminophenol, dichloroaminophenol, etc.); on hydroxyquinoline; on catechol (catechol, dihydroxyflavone, hydroxyflavone, etc.); on resorufin; on chlorophenol red; on fluorescein; on naphthol (alpha-naphthol, 2-naphthol, naphthol-ASBI, etc.); on aminocoumarin (7-amino-4-methylcoumarin, etc.); on naphthylamide; on acridine (aminophenylacridine, etc.); or on aminophenoxazine (aminobenzophenoxazinone, aminopentylresorufin, etc.).

By way of indication, the substrates used for detecting a beta-glucuronidase activity may in particular be 4-methylumbelliferyl-beta-glucuronide, 5-bromo-4-chloro-3-indolyl-beta-glucuronide, 5-bromo-6-chloro-3-indolyl-beta-glucuronide, 6-chloro-3-indolyl-beta-glucuronide, alizarine-beta-glucuronide or cyclohexenoesculetin-beta-glucuronide, or salts thereof.

The substrates used for detecting a beta-galactosidase activity may in particular be 4-methylumbelliferyl-beta-galactoside, 5-bromo-4-chloro-3-indolyl-beta-galactoside, 5-bromo-6-chloro-3-indolyl-beta-galactoside, 6-chloro-3-indolyl-beta-galactoside, alizarine-beta-galactoside or cyclohexenoesculetin-beta-galactoside, or salts thereof.

The substrates used for detecting a beta-glucosidase activity may in particular be 4-methylumbelliferyl-beta-glucoside, 5-bromo-4-chloro-3-indolyl-beta-glucoside, 5-bromo-6-chloro-3-indolyl-beta-glucoside, 6-chloro-3-indolyl-beta-glucoside, alizarine-beta-glucoside, cyclohexenoesculetin-beta-glucoside, nitrophenyl-beta-glucoside or dichloroaminophenylglucoside, or salts thereof.

As an alpha-galactosidase substrate, mention may be made of 4-methylumbelliferyl-alpha-galactoside, 5-bromo-4-chloro-3-indolyl-alpha-galactoside, 5-bromo-6-chloro-3-indolyl-alpha-galactoside, 6-chloro-3-indolyl-alpha-galactoside, alizarine-alpha-galactoside or nitrophenyl-alpha-galactoside or salts thereof.

The expression enzyme A or C, expressed by the majority of *E. coli* is intended to mean an enzyme which is expressed by more than 80% of the *E. coli* under given conditions.

Those skilled in the art are aware of a large number of activities expressed by the majority of *E. coli* strains. Some are in particular described in the Manual of Clinical Microbiology, 7th edition (P. R. Murray and al. 1999), and also in the bioMérieux identification products databases (api 20E, ID 32E, rapid ID 32, etc.)

By way of an enzyme expressed by the majority of *E. coli*, mention may in particular be made of beta-glucuronidase, alpha-galactosidase, beta-ribosidase, phosphatase, L-alanine aminopeptidase, L-leucine aminopeptidase, beta-galactosidase, lactose acidification enzyme, or tryptophanase.

The expression enzyme B, not expressed by the majority of *E. coli* is intended to mean an enzyme which is expressed by less than 20% of the *E. coli* under given conditions.

These activities are also known to those skilled in the art and some of them are described in the documents mentioned above. Mention may in particular be made of beta-glucosidase, N-acetylhexosaminidase, esterase, sulfatase, beta-cellobiosidase, alpha-glucosidase, deaminase, oxydase, pigment synthesis enzyme, beta-alanine aminopeptidase, or elastase.

The term indole test is intended to mean a test which makes it possible to detect the production of indole by microorganisms. In general, the indole produced in a reaction medium is detected by means of a reagent, such as Kovac's reagent, dimethylamino-cinnamaldehyde (DMACA) or James' reagent. In the presence of indole, a red coloration is obtained with Kovac's reagent and James' reagent and a blue coloration is obtained with DMACA.

The term inducer is intended to mean a compound which induces an increase in the expression of the targeted metabolic activity; all experimental conditions being otherwise equal, the metabolic activity is greater when the inducer is at an appropriate concentration than when it is absent or at an unsuitable concentration.

Mention may in particular be made:
for beta-glucuronidase, of a glucuronide preferably selected from glucuronate and methyl-beta-glucuronide;
for beta-galactosidase, of a beta-galactoside preferably selected from lactose and isopropyl-beta-thiogalactoside;
for beta-glucosidase, of a carbohydrate constituted of a carbohydrate linked in the β-position to the glucose, or a carbohydrate with a β-glucoside subunit, in particular cellobiose, cellulose, starch, cellotriose or trehalose. Mention may also be made of methyl-β-glucoside, isopropyl-β-thioglucoside, indoxyl-β-glucoside or methyl-β-thioglucoside;
for alpha-galactosidase, of an alpha-galactoside preferably selected from melibiose and methyl-alpha-galactoside.

In this respect, the invention relates to a method for detecting and/or identifying *Escherichia coli* (*E. coli*) in a biological sample, that comprises:
a) inoculating the biological sample liable to contain *E. coli* on a detection medium that comprises tryptophan and a substrate for an enzyme A, expressed by the majority of *E. coli*, in order to obtain bacterial colonies;
b) detecting the colonies expressing the activity of the enzyme A and identifying them as being *E. coli*; and
c) detecting the colonies that do not express the activity of the enzyme A, carrying out an indole test, and identifying the colonies having a positive indole test as being *E. coli*.

The inoculation of the microorganisms can be carried out by any of the inoculation techniques known to those skilled in the art. An incubation step may be carried out at a temperature for which the enzymatic activity that it is desired to detect is optimal, it being possible for those skilled in the art to readily select this temperature according to the enzymatic activity to be detected. The detection/identification can be carried out by means of a visual examination, by colorimetry or by fluorimetry.

According to one preferred embodiment of the invention, the enzyme A is selected from beta-glucuronidase, alpha-galactosidase, beta-ribosidase, phosphatase, L-alanine aminopeptidase, L-leucine aminopeptidase and beta-galactosidase.

According to one preferred embodiment of the invention, the enzyme A is beta-glucuronidase. Preferably, the substrate for beta-glucuronidase activity is selected from 4-methylumbelliferyl-beta-glucuronide, 5-bromo-4-chloro-3-indolyl-beta-glucuronide, 5-bromo-6-chloro-3-indolyl-beta-glucuronide, 6-chloro-3-indolyl-beta-glucuronide, alizarine-beta-glucuronide or cyclohexenoesculetin-beta-glucuronide, or salts thereof, at concentrations of preferably between 20 and 1000 mg/l.

According to another preferred embodiment of the invention, the enzyme A is beta-galactosidase. Preferably, the substrate for beta-galactosidase activity is selected from 4-methylumbelliferyl-beta-galactoside, 5-bromo-4-chloro-3-indolyl-beta-galactoside, 5-bromo-6-chloro-3-indolyl-beta-galactoside, 6-chloro-3-indolyl-beta-galactoside, alizarine-beta-galactoside or cyclohexenoesculetin-beta-galactoside, or salts thereof, at a concentration of preferably between 10 and 1000 mg/l, preferably between 20 and 500 mg/l.

Preferably, the substrate for said enzyme A is at a concentration of between 10 and 1000 mg/l, preferably between 20 and 500 mg/l.

According to one preferred embodiment of the invention, the tryptophan concentration is greater than or equal to 0.02 g/l, preferably greater than or equal to 0.4 g/l.

According to one preferred embodiment of the invention, the detection medium also comprises a substrate for an enzyme B, not expressed by the majority of E. coli.

According to one preferred embodiment of the invention, the enzyme B is selected from beta-glucosidase, N-acetylhexosaminidase, esterase, sulfatase, beta-cellobiosidase, alpha-glucosidase, deaminase, oxydase, pigment synthesis enzyme, beta-alanine aminopeptidase and elastase.

Preferably, the enzyme B is beta-glucosidase.

Preferably, the substrate for beta-glucosidase activity is selected from 4-methylumbelliferyl-beta-glucoside, 5-bromo-4-chloro-3-indolyl-beta-glucoside, 5-bromo-6-chloro-3-indolyl-beta-glucoside, 6-chloro-3-indolyl-beta-glucoside, alizarine-beta-glucoside, cyclohexenoesculetin-beta-glucoside, nitrophenyl-beta-glucoside or dichloroaminophenylglucoside, or salts thereof, at a concentration of preferably between 10 and 1000 mg/l, preferably between 20 and 500 mg/l.

Preferably, the substrate for said enzyme B is at a concentration of between 10 and 1000 mg/l, preferably between 20 and 500 mg/l.

According to one preferred embodiment of the invention, the detection medium also comprises a substrate for an enzyme C, expressed by the majority of E. coli.

Two embodiments are then possible:
either the enzyme C is identical to the enzyme A; in this case, the substrate should be different. As enzymes A and C, mention may, for example, be made of beta-galactosidase; in this case, the medium comprises, for example, 4-methylumbelliferyl-beta-glucuronide as substrate for the enzyme A, and 5-bromo-6-chloro-3-indolyl-beta-glucuronide as substrate for the enzyme C;
or the enzyme C is different than the enzyme A; mention may for example be made of beta-galactosidase as enzyme A, in combination with alpha-galactosidase as enzyme C. Mention may also be made of beta-galactosidase as enzyme A, in combination with beta-glucuronidase as enzyme C.

Preferably, the enzyme C is selected from beta-glucuronidase, alpha-galactosidase, beta-ribosidase, phosphatase, L-alanine aminopeptidase, L-leucine aminopeptidase, beta-galactosidase.

Preferably, the enzyme C is beta-glucuronidase. Preferably, the substrate for beta-glucuronidase activity is selected from 4-methylumbelliferyl-beta-glucuronide, 5-bromo-4-chloro-3-indolyl-beta-glucuronide, 5-bromo-6-chloro-3-indolyl-beta-glucuronide, 6-chloro-3-indolyl-beta-glucuronide, alizarine-beta-glucuronide or cyclohexenoesculetin-beta-glucuronide, or salts thereof, at concentrations of preferably between 10 and 1000 mg/l.

Preferably, the enzyme C is alpha-galactosidase. Preferably, the substrate for alpha-galactosidase activity is selected from 4-methylumbelliferyl-alpha-galactoside, 5-bromo-4-chloro-3-indolyl-alpha-galactoside, 5-bromo-6-chloro-3-indolyl-alpha-galactoside, 6-chloro-3-indolyl-alpha-galactoside, alizarine-alpha-galactoside or nitrophenyl-alpha-galactoside at concentrations of between 10 and 1000 mg/l/, preferably between 20 and 500 mg/l.

Preferably, the substrate for said enzyme C is at a concentration of between 10 and 1000 mg/l, preferably between 20 and 500 mg/l.

According to one preferred embodiment of the invention, the enzyme A is beta-galactosidase; the enzyme B is beta-glucosidase and the enzyme C is alpha-galactosidase.

In this particular embodiment of the invention,
the substrate for the enzyme A is preferably 5-bromo-4-chloro-3-indolyl-beta-galactoside, 5-bromo-6-chloro-3-indolyl-beta-galactoside, 6-chloro-3-indolyl-beta-galactoside or alizarine-beta-galactoside, at a concentration of between 10 and 1000 mg/l,
the substrate for the enzyme B is preferably 5-bromo-4-chloro-3-indolyl-beta-glucoside, 5-bromo-6-chloro-3-indolyl-beta-glucoside, 6-chloro-3-indolyl-beta-glucoside or alizarine-beta-glucoside, at a concentration of between 10 and 1000 mg/l,
the substrate for the enzyme C is preferably 5-bromo-4-chloro-3-indolyl-alpha-galactoside, 5-bromo-6-chloro-3-indolyl-alpha-galactoside, 6-chloro-3-indolyl-alpha-galactoside or alizarine-alpha-galactoside, at a concentration of between 10 and 1000 mg/l.

According to another preferred embodiment of the invention, the enzyme A is beta-galactosidase; the enzyme B is beta-glucosidase and the enzyme C is beta-glucuronidase.

In this particular embodiment of the invention,
the substrate for the enzyme A is preferably 5-bromo-4-chloro-3-indolyl-beta-galactoside, 5-bromo-6-chloro-3-indolyl-beta-galactoside, 6-chloro-3-indolyl-beta-galactoside or alizarine-beta-galactoside, at a concentration of between 10 and 1000 mg/l,
the substrate for the enzyme B is preferably 5-bromo-4-chloro-3-indolyl-beta-glucoside, 5-bromo-6-chloro-3-indolyl-beta-glucoside, 6-chloro-3-indolyl-beta-glucoside or alizarine-beta-glucoside, at a concentration of between 10 and 1000 mg/l,
the substrate for the enzyme C is preferably 5-bromo-4-chloro-3-indolyl-beta-glucuronide, 5-bromo-6-chloro-3-indolyl-beta-glucuronide, 6-chloro-3-indolyl-beta-glucuronide or alizarine-beta-glucuronide, at a concentration of between 10 and 1000 mg/l.

According to one particular embodiment of the invention, the detection medium also comprises an inducer of the enzyme A, an inducer of the enzyme B and/or an inducer of the enzyme C.

According to one preferred embodiment of the invention, the inducer of the enzyme A, B or C is at a concentration of between 100 ng/l and 10 g/l, preferably between 10 mg/l and 3 g/l.

When the enzyme A or C is beta-glucuronidase, the inducer of said enzyme A or C is preferably a glucuronide, preferably selected from glucuronate and methyl-beta-glucuronide.

When the enzyme A or C is beta-galactosidase, the inducer of said enzyme A or C is preferably a beta-galactoside, preferably selected from lactose and isopropyl-beta-thiogalactoside.

When the enzyme B is beta-glucosidase, the inducer of the enzyme B is preferably a beta-glucoside, preferably selected from methyl-beta-glucose, cellobiose, cellotriose, trehalose, cellulose and starch. Preferably, the inducer of the enzyme B is cellobiose, at a concentration of preferably between 10 mg/l and 10 g/l.

When the enzyme C is alpha-galactosidase, the inducer of the enzyme C is preferably melibiose or methyl-alpha-galactoside.

The invention also relates to a detection medium comprising tryptophan, a substrate for a beta-galactosidase enzyme, a substrate for a beta-glucosidase enzyme, and cellobiose.

According to one preferred embodiment of the invention, the tryptophan concentration is greater than or equal to 0.02 g/l, preferably greater than or equal to 0.4 g/l.

Preferably, the substrate for beta-glucosidase activity is selected from 4-methyl-umbelliferyl-beta-glucoside, 5-bromo-4-chloro-3-indolyl-beta-glucoside, 5-bromo-6-chloro-3-indolyl-beta-glucoside, 6-chloro-3-indolyl-beta-glucoside, alizarine-beta-glucoside, cyclohexenoesculetinbeta-glucoside, nitrophenyl-beta-glucoside or dichloroaminophenylglucoside, or salts thereof, at a concentration of preferably between 10 and 1000 mg/l, preferably between 20 and 500 mg/l.

Preferably, the substrate for beta-galactosidase activity is selected from 4-methylumbelliferyl-beta-galactoside, 5-bromo-4-chloro-3-indolyl-beta-galactoside, 5-bromo-6-chloro-3-indolyl-beta-galactoside, 6-chloro-3-indolyl-beta-galactoside, alizarine-beta-galactoside or cyclohexenoescu-letin-beta-galactoside, or salts thereof, at a concentration of preferably between 10 and 1000 mg/l, preferably of between 20 and 500 mg/l.

Preferably, the cellobiose is at a concentration of between 10 mg/l and 10 g/l.

According to one preferred embodiment of the invention, the detection medium also comprises a substrate for an alpha-galactosidase enzyme.

As a substrate for alpha-galactosidase, mention may in particular be made of 4-methylumbelliferyl-alpha-galacto-side, 5-bromo-4-chloro-3-indolyl-alpha-galactoside, 5-bromo-6-chloro-3-indolyl-alpha-galactoside, 6-chloro-3-indolyl-alpha-galactoside, alizarine-alpha-galactoside or nitrophenyl-alpha-galactoside, at concentrations of between 20 and 1000 mg/l/.

The invention also relates to the use of a medium as defined above, for detecting *E. coli*.

The examples below are given by way of explanation and are in no way limiting in nature. They will make it possible to understand the invention more clearly.

EXAMPLE 1

Contribution of the Indole Test on Colorless Colonies for Detecting *Escherichia coli*

Three thousand (3000) urine samples were inoculated on the commercially available CPS ID 3 medium (bioMérieux). The media were incubated and analyzed in accordance with the supplier's recommendations: for detecting and identifying *Escherichia coli* strains, the pink-to-red colonies were pre-identified as belonging to the *E. coli* species. An indole test was carried out in order to confirm this identification. In parallel, the media were used and analyzed in accordance with the present invention: the pink-to-red colonies were identified as belonging to the *E. coli* species; an indole test was carried out on the colorless colonies; if the reaction was positive, the strain was identified as *E. coli*.

All the identifications were confirmed using suitable biochemical tests commonly used by medical test laboratories.

TABLE 1

Contribution of the indole test on colorless colonies for identifying
*E. coli* strains on CPS ID 3 medium

|  |  | *E. coli* identification sensitivity |
|---|---|---|
| Method of the supplier | without indole test | 94% |
|  | with indole test on pink-to-red colonies | 90% |
| According to the invention | with indole test on colorless colonies | 99.9% |

It is very clear from Table 1 that, when the indole test is carried out only on the pink-to-red colonies on CPS ID 3 medium, as proposed by the supplier, this results in a decrease in the sensitivity of identification of the *E. coli* strains. On the other hand, if this test is carried out on the colorless colonies, this makes it possible to obtain a very high identification sensitivity.

EXAMPLE 2

Contribution of the Indole Test on a Medium Combining Cellobiose, 6-chloro-3-indolyl-β-glucuronide, 5-bromo-6-chloro-3-indolyl-β-galactoside and 5-bromo-4-chloro-3-indolyl-β-glucoside Tryptophan, 6-chloro-3-indolyl-β-glucuronide, 5-bromo-6-chloro-3-indolyl-β-galactoside and 5-bromo-4-chloro-3-indolyl-β-glucoside are added, 0.9 g/l, 0.15 g/l, 0.05 g/l and 0.1 g/l respectively, to Trypticase Soy Agar medium (bioMérieux). This medium is supplemented, or not supplemented, with cellobiose at 0.5 g/l. These two media are distributed in a proportion of 20 ml per Petri dish. Microorganisms commonly isolated from urine samples and derived from the applicant's collection are inoculated on these media by semi-quantitative isolation of 10 μl of a suspension at 0.5 McFarland, diluted to 1/20. The dishes are incubated at 37° C. for 24 hours, and then the colonies formed are examined visually. The coloration of these colonies is noted. An indole test is carried out on the colorless colonies using James' reagent (bioMérieux). The results are given in Table 2 below:

TABLE 2

Contribution of the indole test on a medium combining 6-chloro-3-indolyl-β-glucuronide, 5-bromo-6-chloro-3-indolyl-β-galactoside and 5-bromo-4-chloro-3-indolyl-β-glucoside, possibly supplemented with cellobiose, on the identification of *E. coli*

|  | Cellobiose concentration in mg/l | | | |
|---|---|---|---|---|
|  | 0 | | 500 | |
| Strains | Colonies | Indole | Colonies | Indole |
| *Escherichia coli* 407 | pink |  | pink |  |
| *Escherichia coli* 067 | pink |  | pink |  |
| *Escherichia coli* 001 | colorless | positive | colorless | positive |
| *Klebsiella pneumoniae* 111 | turquoise |  | turquoise |  |
| *Serratia marcescens* 112 | turquoise |  | turquoise |  |
| *Citrobacer freundii* 031 | gray |  | gray |  |
| *Citrobacter freundii* 009 | pink |  | violet |  |
| *Streptococcus agalactiae* 019 | mauve |  | mauve |  |
| *Enterococcus faecalis* 117 | turquoise |  | turquoise |  |

It is clear from Table 2 above that, in a medium combining tryptophan, 6-chloro-3-indolyl-β-glucuronide, 5-bromo-6-chloro-3-indolyl-β-galactoside and 5-bromo-4-chloro-3-indolyl-β-glucoside, cellobiose makes it possible to differentiate more clearly between the *Citrobacter* 009 strain and the *E. coli* strains. Moreover, in the presence of tryptophan, searching for the production of indole by the colorless colonies makes it possible to further increase the sensitivity for detecting *E. coli* without being penalized by damage to the specificity.

EXAMPLE 3

Impact of the Tryptophan Concentration on the Detection of the Colorless Colonies if *E. coli*

Various concentrations of tryptophan (0-0.3-0.6-0.9 g/l) and also cellobiose at 100 mg/l are added to the CPS ID 3 medium (bioMérieux). These media contain 6-chloro-3-indolyl-beta-glucuronide at 250 mg/l and 5-bromo-4-chloro-3-indolyl-beta-glucoside at 50 mg/l. These media are distributed in a proportion of 20 ml per Petri dish. Microorganisms derived from the applicant's collection were inoculated on these media by semi-quantitative isolation of 10 μl of a suspension at 0.5 McFarland, diluted to ½0. The dishes were incubated at 37° C. for 24 hours. The colonies formed were examined visually after 24 hours of incubation. The coloration of these colonies is noted. An indole test is carried out on the colorless colonies using James' reagent (bioMérieux). The results are given in Table 3 below:

TABLE 3

Impact of tryptophan concentration on the detection of colorless colonies of *E. coli*

| Strain | Tryptophan concentration in g/l | | | | | |
|---|---|---|---|---|---|---|
| | 0.3 | | 0.6 | | 0.9 | |
| | Colonies | Indole | Colonies | Indole | Colonies | Indole |
| *Escherichia coli* 407 | pink | | pink | | pink | |
| *Escherichia coli* 067 | pink | | pink | | pink | |
| *Escherichia coli* 001 | colorless | weak | colorless | positive | colorless | positive |
| *Klebsiella pneumoniae* 111 | turquoise | | turquoise | | turquoise | |
| *Serratia marcescens* 112 | turquoise | | turquoise | | turquoise | |
| *Citrobacter freundii* 031 | gray | | gray | | gray | |
| *Citrobacter freundii* 009 | pink | | pink | | violet | |
| *Streptococcus agalactiae* 019 | mauve | | mauve | | mauve | |
| *Enterococcus faecalis* 117 | turquoise | | turquoise | | turquoise | |

It is clear from Table 3 above that, even with a tryptophan concentration of 0.3 g/l, it is possible to detect the production of indole by the *E. coli* strains; nevertheless, the reaction is more marked at higher concentrations.

EXAMPLE 4

Contribution of the Indole Test on a Medium Combining Cellobiose, 5-bromo-6-chloro-3-indolyl-alpha-galactoside, 5-bromo-6-chloro-3-indolyl-β-galactoside and 5-bromo-4-chloro-3-indolyl-β-glucoside 5-Bromo-6-chloro-3-indolyl-alpha-galactoside, 5-bromo-6-chloro-3-indolyl-β-galactoside, 5-bromo-4-chloro-3-indolyl-β-glucoside and isopropyl-thio-β-galactoside are added, at 75 mg/l, 50 mg/l, 50 mg/l and 10 mg/l respectively, to CPS ID 3 medium (bioMérieux) from which the synthetic enzymatic substrates have been removed. This medium is distributed in a proportion of 20 ml per Petri dish. Microorganisms derived from the applicant's collection were inoculated on this medium by semi-quantitative isolation of 10 μl of a suspension at 0.5 McFarland, diluted to ½0. The dishes were incubated at 37° C. for 24 hours. The colonies formed were examined visually after 24 hours of incubation. The coloration of these colonies is noted. An indole test is carried out on the colorless colonies using James' reagent (bioMérieux). The results are given in Table 4 below:

TABLE 4

Impact of tryptophan concentration on the detection of colorless colonies of *E. coli*

| Strain | Colonies | Indole |
|---|---|---|
| *Escherichia coli* 407 | red | |
| *Escherichia coli* 003 | red | |
| *Escherichia coli* 051 | colorless | positive |
| *Klebsiella pneumoniae* 043 | blue | |
| *Serratia marcescens* 112 | turquoise | |
| *Citrobacer freundii* 025 | violet | |
| *Streptococcus agalactiae* 003 | turquoise | |
| *Enterococcus faecalis* 117 | turquoise | |

It is clear from Table 4 above that, in a medium combining 5-bromo-6-chloro-3-indolyl-alpha-galactoside, 5-bromo-6-chloro-3-indolyl-β-galactoside and 5-bromo-4-chloro-3-indolyl-β-glucoside, the production of indole by the colorless colonies makes it possible to increase the sensitivity for detecting *E. coli*.

The invention claimed is:

1. A method for detecting and/or identifying *Escherichia coli* (*E. coli*) in a biological sample, the method comprising:
   a) inoculating the biological sample liable to contain *E. coli* on a detection medium that comprises:
      tryptophan and a reagent for spontaneously detecting deaminase activity,
      a substrate for an enzyme A, wherein enzyme A is expressed by a majority of *E. coli*, and
      a substrate for an enzyme B that is not expressed by a majority of *E. coil*,
   in order to obtain bacterial colonies;
   b) detecting the colonies expressing enzyme A activity and identifying them as being *E. coli*; and
   c) detecting colonies that do not express enzyme A activity, nor deaminase activity, nor enzyme B activity, carrying out an indole test only on the colonies that do not express enzyme A activity, nor deaminase activity, nor enzyme B activity, and identifying the colonies having a positive indole test as being *E. coli*.

2. The method as claimed in claim 1, wherein a tryptophan concentration of the detection medium is greater than or equal to 0.02 g/l.

3. The method as claimed in claim 1, wherein the detection medium further comprises:
a substrate for an enzyme C that is expressed by the majority of *E. coli*.

4. The method as claimed in claim 1, wherein the enzyme A is selected from beta-glucuronidase, alpha-galactosidase, beta-ribosidase, phosphatase, L alanine aminopeptidase, L-leucine aminopeptidase, and beta-galactosidase.

5. The method as claimed in claim 1, wherein the enzyme A is beta-glucuronidase or beta-galactosidase.

6. The method as claimed in claim 1, wherein the enzyme B is selected from beta-glucosidase, N-acetylhexosaminidase, esterase, sulfatase, beta-xylosidase, phospholipase, alpha-mannosidase, beta-mannosidase, beta-cellobiosidase, alpha-glucosidase, deaminase, oxydase, pigment synthesis enzyme, beta-alanine aminopeptidase, and elastase.

7. The method as claimed in claim 6, wherein the enzyme B is beta-glucosidase.

8. The method as claimed in claim 3, wherein the enzyme C is selected from beta-glucuronidase, alpha-galactosidase, beta-ribosidase, phosphatase, L alanine aminopeptidase, L-leucine aminopeptidase, and beta-galactosidase.

9. The method as claimed in claim 3, wherein the enzyme A is beta-galactosidase; the enzyme B is beta-glucosidase; and the enzyme C is alpha-galactosidase.

10. The method as claimed in claim 3, wherein the enzyme A is beta-galactosidase; the enzyme B is beta-glucosidase; and the enzyme C is beta-glucuronidase.

11. The method as claimed in claim 3, wherein the detection medium further comprises an inducer of the enzyme A, an inducer of the enzyme B and/or an inducer of the enzyme C.

12. The method as claimed in claim 11, wherein the enzyme A is beta-glucuronidase and the inducer of said enzyme A is a glucuronide.

13. The method as claimed in claim 11, wherein the enzyme A is beta-galactosidase and the inducer of said enzyme A is a beta-galactoside.

14. The method as claimed in claim 11, wherein the enzyme B is beta-glucosidase and the inducer of the enzyme B is a beta-glucoside.

15. The method as claimed in claim 11, wherein the enzyme B is beta-glucosidase and the inducer of the enzyme B is cellobiose.

16. A method of detecting *E. coli* in a biological sample, the method comprising:
a) inoculating the biological sample liable to contain *E. coli* on a detection medium that comprises:
tryptophan and a reagent for spontaneously detecting deaminase activity,
a substrate for a beta-galactosidase enzyme,
a substrate for a beta-glucosidase enzyme, and
cellobiose as an inducer in a concentration in a range of from 10 mg/l to 3 g/l,
in order to obtain bacterial colonies; and
b) detecting colonies of *E. coli*.

* * * * *